United States Patent
Wilker et al.

(10) Patent No.: US 7,106,058 B2
(45) Date of Patent: Sep. 12, 2006

(54) DETECTION OF CONTRABAND USING NUCLEAR QUADRUPOLE RESONANCE

(75) Inventors: Charles Wilker, Wilmington, DE (US); James D. McCambridge, Swarthmore, PA (US)

(73) Assignee: E.I. Dupont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/985,112

(22) Filed: Nov. 10, 2004

(65) Prior Publication Data

US 2005/0122109 A1   Jun. 9, 2005

Related U.S. Application Data

(60) Provisional application No. 60/519,127, filed on Nov. 12, 2003.

(51) Int. Cl.
*G01V 3/00* (2006.01)

(52) U.S. Cl. .................................... 324/300; 324/307

(58) Field of Classification Search ............... 324/300, 324/307, 309, 312, 314, 318, 322
See application file for complete search history.

(56) References Cited

U.S. PATENT DOCUMENTS

| | | | |
|---|---|---|---|
| 4,514,691 A | | 4/1985 | De Los Santos et al. |
| 5,036,279 A | * | 7/1991 | Jonsen .................. 324/307 |
| 5,206,592 A | * | 4/1993 | Buess et al. ............ 324/307 |
| 5,233,300 A | | 8/1993 | Buess et al. |
| 5,262,394 A | | 11/1993 | Wu et al. |
| 5,276,398 A | | 1/1994 | Withers et al. |
| 5,351,007 A | | 9/1994 | Withers et al. |
| 5,457,385 A | | 10/1995 | Sydney et al. |
| 5,571,146 A | | 11/1996 | Jones et al. |
| 5,583,437 A | | 12/1996 | Smith et al. |
| 5,585,723 A | | 12/1996 | Withers |
| 5,592,083 A | | 1/1997 | Magnuson et al. |
| 5,594,338 A | | 1/1997 | Magnuson |
| 5,656,937 A | | 8/1997 | Cantor |
| 5,661,400 A | | 8/1997 | Plies et al. |
| 5,750,473 A | | 5/1998 | Shen |
| 5,804,967 A | | 9/1998 | Miller et al. |
| 5,814,987 A | | 9/1998 | Smith et al. |
| 5,814,989 A | | 9/1998 | Smith et al. |
| 5,973,495 A | | 10/1999 | Mansfield |
| 5,986,455 A | | 11/1999 | Magnuson |
| 5,999,000 A | | 12/1999 | Srinivasan |
| 6,025,719 A | | 2/2000 | Anderson |
| 6,054,856 A | | 4/2000 | Garroway et al. |
| 6,091,240 A | | 7/2000 | Smith et al. |
| 6,104,190 A | | 8/2000 | Buess et al. |
| 6,108,569 A | | 8/2000 | Shen |

(Continued)

FOREIGN PATENT DOCUMENTS

EP    0 426 851    5/1991

(Continued)

OTHER PUBLICATIONS

A.N. Garroway, et al., "Narcotics and expolosives detection by N pure NQR", SPIE (1993) pp. 318-327) vol. 2092, Maryland.

(Continued)

*Primary Examiner*—Louis M. Arana

(57) ABSTRACT

This invention relates to the use of a nuclear quadrupole resonance detection system for detecting contraband, wherein the detection system comprises a container with a detection panel and at least one coil for exciting and detecting the nuclear quadrupole resonance frequencies of a contraband source placed near an outer side of the detection panel.

12 Claims, 3 Drawing Sheets

U.S. PATENT DOCUMENTS

| | | | |
|---|---|---|---|
| 6,150,816 | A | 11/2000 | Srinivasan |
| 6,166,541 | A | 12/2000 | Smith et al. |
| 6,169,399 | B1 | 1/2001 | Zhang et al. |
| 6,194,898 | B1 | 2/2001 | Magnuson et al. |
| 6,201,392 | B1 | 3/2001 | Anderson et al. |
| 6,218,943 | B1 | 4/2001 | Ellenbogen |
| 6,242,918 | B1 | 6/2001 | Miller et al. |
| 6,291,994 | B1 | 9/2001 | Kim et al. |
| 6,335,622 | B1 | 1/2002 | James et al. |
| 6,370,404 | B1 | 4/2002 | Shen |
| D459,245 | S | 6/2002 | Power |
| 6,420,872 | B1 | 7/2002 | Garroway et al. |
| 6,486,838 | B1 | 11/2002 | Smith et al. |
| 6,538,445 | B1 | 3/2003 | James et al. |
| 6,556,013 | B1 * | 4/2003 | Withers ............ 324/322 |
| 6,566,873 | B1 | 5/2003 | Smith et al. |
| 6,590,394 | B1 | 7/2003 | Wong et al. |
| 6,751,489 | B1 | 6/2004 | Shen |
| 6,777,937 | B1 * | 8/2004 | Miller et al. .......... 324/318 |
| 6,819,109 | B1 | 11/2004 | Sowers et al. |
| 2002/0068682 | A1 | 6/2002 | Shen |
| 2002/0153891 | A1 | 10/2002 | Smith et al. |
| 2002/0169374 | A1 | 11/2002 | Jevtic |
| 2002/0190715 | A1 | 12/2002 | Marek |
| 2003/0062896 | A1 | 4/2003 | Wong et al. |
| 2003/0071619 | A1 | 4/2003 | Sauer et al. |
| 2004/0222790 | A1 | 11/2004 | Karmi et al. |

FOREIGN PATENT DOCUMENTS

| | | |
|---|---|---|
| EP | 1 168 483 | 1/2002 |
| GB | 2 286 248 | 8/1995 |
| GB | 2289 344 | 11/1995 |
| WO | WO 92/19978 | 11/1992 |
| WO | WO 92/21989 | 12/1992 |
| WO | WO 94/05022 | 3/1994 |
| WO | WO 95/34096 | 12/1995 |
| WO | WO 96/37438 | 11/1996 |
| WO | WO 96/39636 | 12/1996 |
| WO | WO 98/37438 | 8/1998 |
| WO | WO 98/54590 | 12/1998 |
| WO | WO 99/45409 | 9/1999 |
| WO | WO 99/50689 | 10/1999 |
| WO | WO 00/70356 | 11/2000 |
| WO | WO 02/098364 | 12/2002 |
| WO | WO 03/014700 | 2/2003 |
| WO | WO 03/040761 | 5/2003 |
| WO | WO 03/096041 | 11/2003 |

OTHER PUBLICATIONS

Garroway, et al., "Remote Sensing by Nuclear Quadrupole Resonance", IEEE Transactions on Geoscience and Remote Sensing, (2001) pp. 1108-1118, vol. 39, No. 6.

T. Hirschfeld, "Short Range Remote NQR Measurements", Journal of Molecular Structure, (1980), p. 63-77, vol. 58, California.

Miller, et al., "Performance of a High-Termperature Superconducting Probe for In Vivo Microscopy at 2.0 T", Magnetic Resonance in Medicine, (1999) pp. 72-79, vol. 41.

W.H. Wong, et al., "HTS Coils for High Resolution Nuclear Magnetic Resonance Spectroscopy", Advances in Cryogenic Engineering, (1996), pp. 953-959, New York.

V. Kotsubo et al., "Cryogenic System for a High Temperature Superconductor NMR Probe", Advances in Cryogenic Engineering, Jul. 17, 1995, vol. 41, pp. 1857-1864, New York.

Kushida, et al., "Dependence on the Pure Quadrupole Resonance Frequency on Pressure and Temperature", Physical Review, (Dec. 1956), pp. 1364-1377, vol. 104, No. 5, Massachusetts.

Vanier, "Temperature Dependence of the Pure Nuclear Quadrupole Resonance Frequency in KC103", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Turner, C.W., High temperature superconductor circuit components for cryogenic microwave systems, Electrical and Computer Engineering, 1993, Canadian Conference on Vancouver, BC Canada (Sep. 14-17, 1993) Sep. 14, 1993 XP 010118071.

W. A. Edelstein et al., A signal-to-noise calibration procedure for NMR imaging systems, Medical Physics, vol. 11 (2) Mar./Apr. 1984, pp. 180-185.

He, D.F. et al., "Metal detector based on high-Tc RF Squid", Physics C 378-381 (2002) pp. 1404-1407.

Wilker, "HTS Sensors for NQR Spectroscopy", Microwave Symposium Digest, vol. 1, pg. 143-146 (2004).

Stensgaard, "Optimized Design of the Shielded-Loop Resonator", Journal of Magnetic Resonance, Series A 122, 120-125 (1996).

* cited by examiner

DETECTION OF CONTRABAND USING NUCLEAR QUADRUPOLE RESONANCE

This application claims the benefit of U.S. Provisional Application No. 60/519,127, filed Nov. 12, 2003, which is incorporated in its entirety as a part hereof for all purposes.

FIELD OF THE INVENTION

This invention relates to a nuclear quadrupole resonance detection system for detecting contraband.

BACKGROUND OF THE INVENTION

The use of nuclear quadrupole resonance (NQR) as a means of detecting explosives and other contraband has been recognized for some time—see e.g. T. Hirshfield et al, *J. Molec. Struct.* 58, 63 (1980); A. N. Garroway et al, *Proc. SPIE* 2092, 318 (1993); and A. N. Garroway et al, *IEEE Trans. on Geoscience and Remote Sensing*, 39, pp. 1108–1118 (2001). NQR provides some distinct advantages over other detection methods. NQR requires no external magnet such as required by nuclear magnetic resonance. NQR is sensitive to the compounds of interest, i.e. there is a specificity of the NQR frequencies.

One technique for measuring NQR in a sample is to place the sample within a solenoid coil that surrounds the sample. The coil provides a radio frequency (RF) magnetic field that excites the quadrupole nuclei in the sample and results in their producing their characteristic resonance signals. This is the typical apparatus configuration that might be used for scanning mail, baggage or luggage. There is also need for an NQR detector that permits detection of NQR signals from a source outside the detector, e.g. a wand detector, that could be passed over persons or containers as is done with existing metal detectors. Problems associated with such a detector using conventional systems are the decrease in detectability with distance from the detector coil and the associated equipment needed to operate the system.

An NQR detection system can have one or more coils that both transmit and receive, or it can have coils that solely transmit or solely receive coil. The transmit, or transmit and receive, coil of the NQR detection system provides a radio frequency (RF) magnetic field that excites the quadrupole nuclei in the sample and results in their producing their characteristic resonance signals that the receive, or transmit and receive, coil detects. The NQR signals have low intensity and short duration. The transmit, receive, or transmit and receive coil is preferably tunable and has a high quality factor (Q). After the RF signal is transmitted, the transmit, receive, or transmit and receive coil will typically experience ringing and it must have a rapid recovery time in order for the receive or transmit and receive coil to be able to detect the low intensity NQR signal. One method of accomplishing this is to use a Q-damping circuit that is activated to provide a rapid recovery.

An object of the present invention is to provide a NQR detector that permits detection of NQR signals from a source outside the detector.

SUMMARY OF THE INVENTION

This invention provides a nuclear quadrupole resonance detection system for detecting contraband comprising a container with a detection panel and at least one coil for exciting and detecting nuclear quadrupole resonance frequencies of a contraband source positioned near an outer side of the detection panel, wherein a coil is within the container and in close proximity to an inner side of the detection panel. Preferably, the nuclear quadrupole resonance detection system contains a sufficient number of coils so that the entire surface region of an object placed near to the outer side of the detection panel can be scanned. These coils can be used to scan, i.e. excite and detect the nuclear quadrupole resonance frequencies, either sequentially or simultaneously. For many applications it is preferable that the detection panel has a flat surface.

In one embodiment the detection panel is positioned vertically so that a person can stand near to or pass by it and be scanned for contraband.

In another embodiment, a flat surface detection panel is positioned horizontally near to the floor so that a person can stand on or walk over the detection panel thereby enabling the efficient detection of contraband contained in a person's shoes without the necessity of removing the shoes from the feet of the person.

In still another embodiment, the detection system is in the form of a portal through which a person to be examined passes.

This detection system is useful for detecting explosives, drugs and other contraband.

BRIEF DESCRIPTION OF THE DRAWINGS

The invention will be more fully understood from the following detailed description, taken in connection with the accompanying drawings, which form a part of this application and in which.

DETAILED DESCRIPTION OF THE INVENTION

Figure 1:
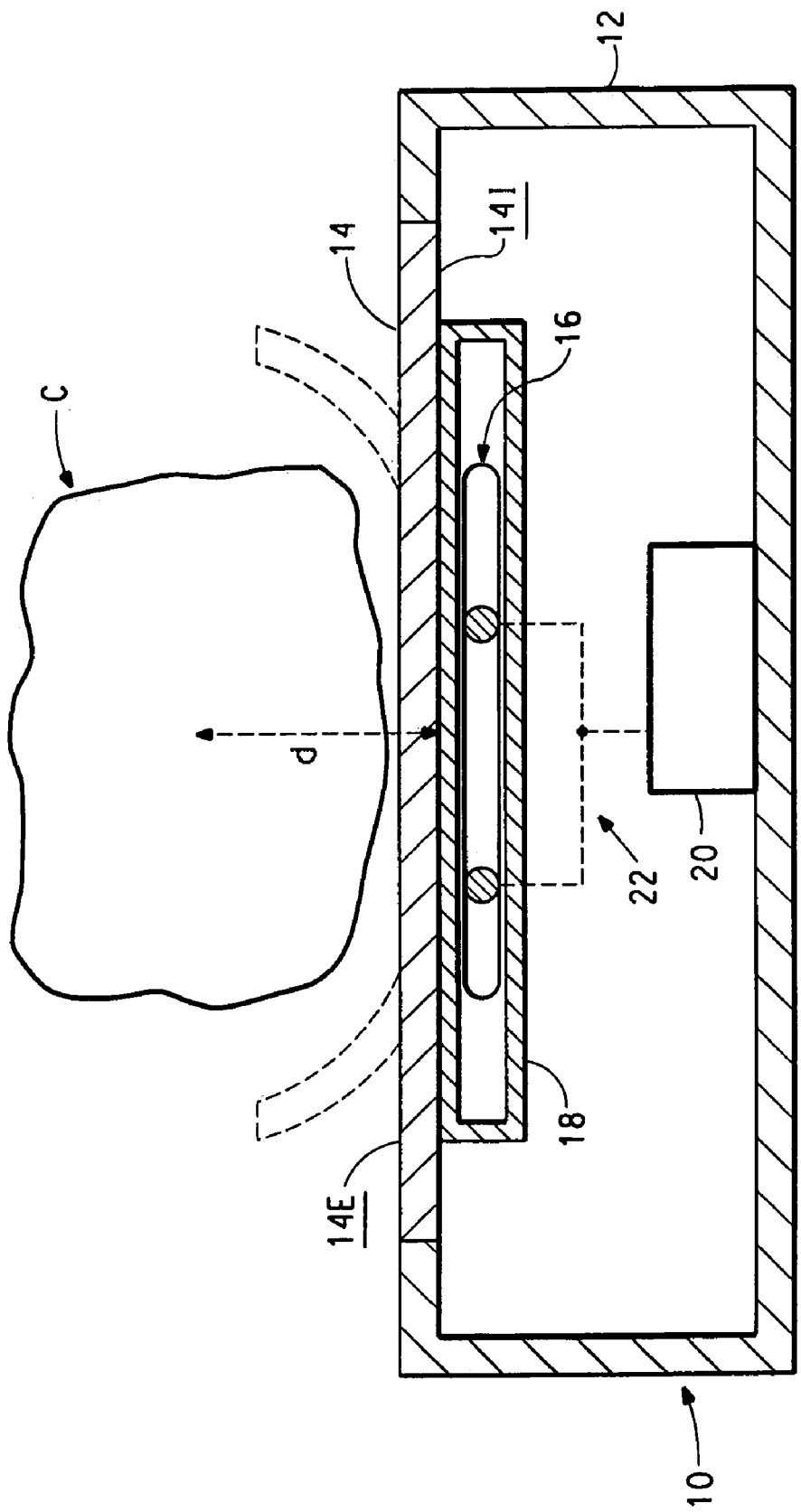
FIG. 1 is a generalized side elevational view, entirely in section, illustrating the elements of the detection system of the present invention.

Throughout the following detailed description similar reference numerals refer to similar elements in all figures of the drawings.

The invention relates to a nuclear quadruple resonance detection system for detecting contraband. As seen from FIG. 1 the nuclear quadruple resonance ("NQR") detection system, generally indicated by the reference numeral 10, comprises a container 12 with a detection panel 14. The panel 14 has an interior surface 14I and an outer surface 14E thereon. The outer surface 14E of the detection panel 14 defines a portion of the exterior of the container 12. The panel 14 may be integrally formed with the other boundary walls of the container, if desired. A person to be examined or a potential source of contraband C is positioned near to this outer surface 14E.

The system 10 includes at least one coil 16 for detecting the nuclear quadruple resonance frequencies of the contraband source C. In accordance with the present invention the coil 16 is a high temperature semiconductor (HTS) coil having a high quality factor ("Q"). The at least one coil 16 is disposed within the interior volume 12V of the container 12 and in close proximity to the inner surface 14I of the detection panel 14.

The coil 16 is disposed is a suitable enclosure 18 such that the coil 16 may be cooled to liquid nitrogen temperature. The power supply and related circuitry are contained in a suitable housing 20 and connected to the coil 16 over a suitable connection 22. As noted herein and as indicated diagrammatically in FIG. 1, the panel 14 maybe arranged in the form of a cylinder with a diameter 2d, where d is the NQR detection distance.

The detection panel can have a flat surface, a curved surface or a surface of some other shape depending on the objects to be examined. For many purposes, a flat surface detection panel is preferred. For some of these embodiments it is desirable that at least one dimension, such as the thickness, of the body of the container in the portion of the container enclosing the detection panel be kept to a minimum. For such embodiments, the thickness or other dimension of the container in the portion of the container with the detection panel is preferably less than about 8 inches (20 cm). More preferably, the thickness or other dimension is less than about 6 inches (15 cm).

This detection system can be used to examine the surface regions of an object placed near to the outer side of the detection panel. If the size of the detection panel and the object to be examined are sufficiently small or if the object to be examined can be translated with respect to the detection panel, a single coil can be used. A single coil can also be used to examine larger objects if means are provided to translate the coil within the container or to translate the object with respect to the coil to thereby scan different areas of the object. Preferably, when the detection system is to be used to scan larger objects, a sufficient number of appropriately placed coils are used to enable the complete scanning of the entire surface region of the object placed near to the outer side of the detection panel. The number and placement of the coils will be dictated by the size of the detection panel and the size of coils. The size of the detection panel will be dictated by the size of the object to be examined.

A sufficient number of appropriately placed coils can easily be determined for a given panel and a given coil size. This can be done by passing a localized source of NQR frequencies across the detection panel and increasing the number of coils that excite NQR frequencies, i.e. transmit the RF pulse, and the number of sensor coils that detect the NQR frequencies, i.e. receive the NQR signals, and spacing them until the signals are received no matter where the source is placed on the detection panel.

If a single coil is used, it must be a transmit and receive coil. Separate coils can be used to solely transmit and solely receive.

The coils used in this invention can be made of copper, silver or a high temperature superconductor. A copper or silver coil is preferably in the form of a shielded loop-resonator (SLR) coil. SLR's have been developed to eliminate the detuning effect of the electrical interaction between the coil and the surrounding material. A SLR coil is preferred as a coil that is used to solely transmit. A copper SLR is especially preferred. When a single coil is used to both transmit and receive, a HTS self-resonant coil is preferred. When separate coils are used to transmit and receive, it is preferred to use HTS self-resonant coils as receive coils to detect the NQR signals. A high temperature superconductor (HTS) coil is preferably in the form of a self-resonant planar coil, i.e. a surface coil, with a coil configuration of HTS on one or both sides of a substrate. High temperature superconductors are those that superconduct above 77 K. The high temperature superconductors used to form the HTS self-resonant coil are preferably selected from the group consisting of $YBa_2Cu_3O_7$, $Tl_2Ba_2CaCu_2O_8$, $TlBa_2Ca_2Cu_3O_9$, $(TlPb)Sr_2CaCu_2O_7$ and $(TlPb)Sr_2Ca_2Cu_3O_9$. Most preferably, the high temperature superconductor is $YBa_2Cu_3O_7$ or $Tl_2Ba_2CaCu_2O_8$.

The use of a HTS self-resonant coil provides several advantages during both the transmit and the receive times over the conventionally used copper coil or of a silver coil. These advantages arise from the high Q of the HTS self-resonant coil, which has Q's on the order of $10^3$–$10^6$ compared to the typical Q of $10^2$ for a copper system. The large Q's of HTS self-resonant coils produce large magnetic field strengths during the RF transmit pulse and do so at lower RF power levels. This dramatically reduces the amount of transmitted power required to produce NQR signals for detection and thereby reduces the size of the RF power supply sufficiently so that it can be run on portable batteries. The large Q of the HTS self-resonant coil also plays an important role during the receive time. The signal-to-noise (S/N) ratio is approximately proportional to the square root of Q so that the use of the HTS self-resonant coil results in an increase in S/N by a factor of 10–100 over that of the copper system.

It is often advantageous to be able to fine tune the resonance frequency. One means for accomplishing such tuning is to use two coupled high temperature superconductor self-resonant coils. The resonance frequency of the fundamental symmetric mode of the two coupled high temperature superconductor self-resonant coils can be varied by mechanically displacing one coil with respect to the other, and these coupled coils serve as the HTS transmit, receive or transmit and receive coil. Preferably, the two coils are planar coils.

Provision must be made for a power supply to supply power for transmitting the RF pulse as well as provision for related circuitry for processing the detected NQR signals. The power supply and related circuitry for processing the detected NQR signals can be contained within the container that also contains the at least one coil for detecting the nuclear quadrupole resonance signals. Alternatively, they can be in one or more separate containers. If one or more HTS coils are used, provision must also be made for cooling the HTS to liquid nitrogen temperature.

The distance from a coil within which NQR frequencies can be detected depends upon the size of the sample, the properties of the coil used, such as coil size, Q and the like, and the related equipment and circuitry used for processing the detected NQR signals. This distance consists of the distance from the coil to the surface of the object to be examined and the depth, "d", of the surface region of the object, i.e. the distance from the surface of the object into the object within which NQR signals with NQR frequencies produced by quadrupole nuclei can be detected by a receive coil. The surface region referred to above is the portion of the surface of the object with depth d within which quadrupole nuclei produce NQR signals that can be detected by a receive coil. In order to maximize the depth of the surface region, it is important to place the object to be examined as close to the coil as possible. For this reason the coil should be placed in as close proximity to the inner side of the detection panel as possible, and the object to be examined should be positioned as close to the outer side of the detection panel as possible.

The detection panel can be in various forms and orientations depending upon the object to be examined.

In one embodiment a flat surface detection panel is positioned vertically so that a person, a human subject, can stand near to or pass by it and be scanned for contraband. The person to be examined is directed to stand as near as possible facing the detection panel and then to stand as near as possible with his or her back to the detection panel. In addition, the person can be instructed to stand sideways with arm raised above the head to enable the body to be as close to the detection panel as possible. This embodiment provides an efficient method of scanning a person for concealed contraband.

Figure 2A:
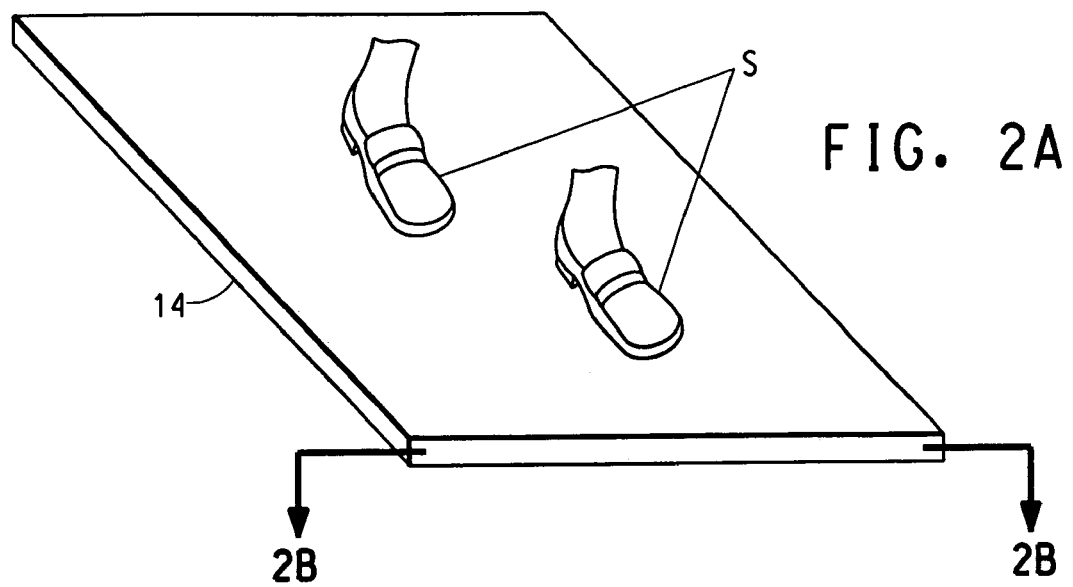
FIGS. 2A and 2B show an embodiment of the present invention for scanning shoes in which a flat surface detection panel is positioned horizontally on the floor, with FIG. 2B being a sectional view taken along section lines 2B—2B in FIG. 2A.
Figure 2B:
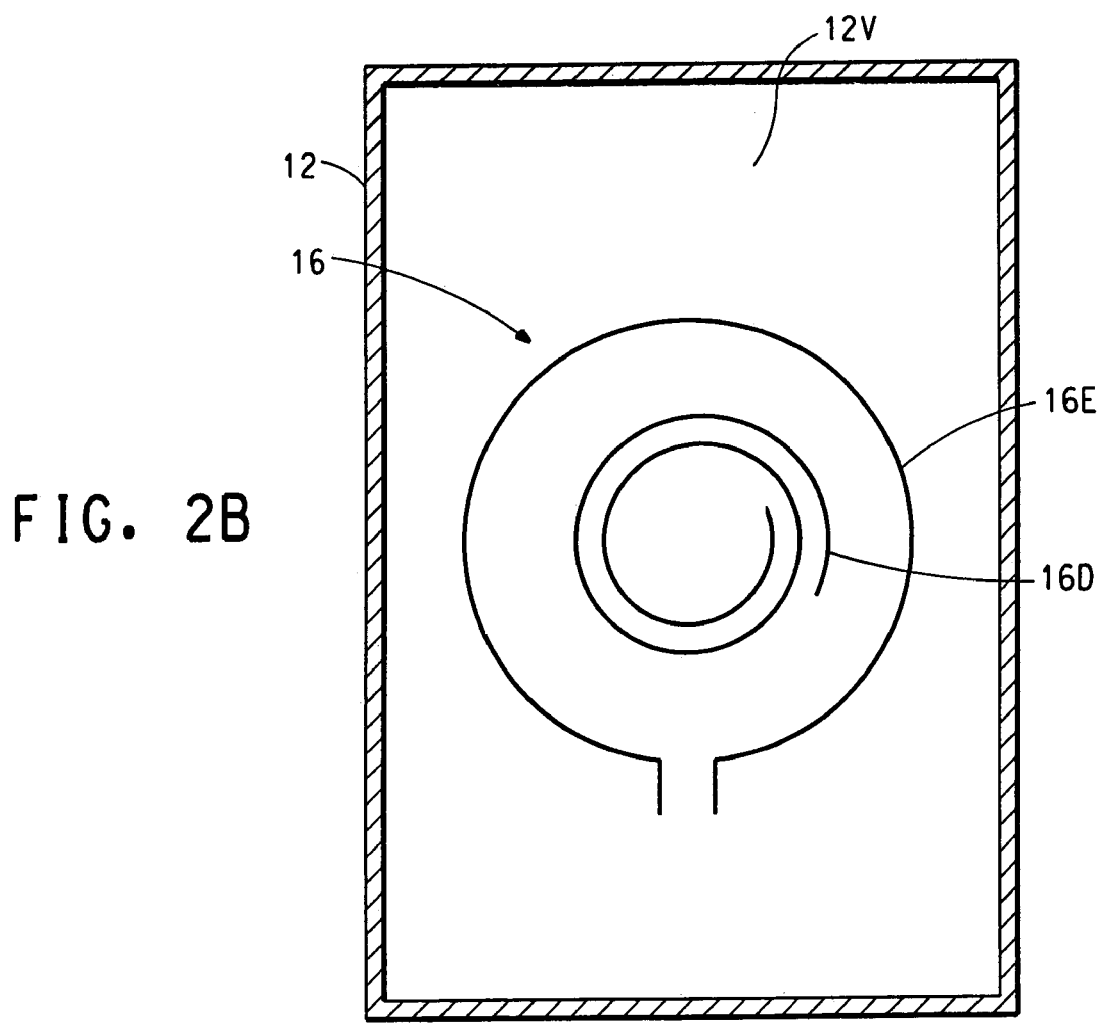

In an alternative embodiment, a flat surface detection panel is positioned horizontally near to the floor so that a person can stand on or walk over the detection panel. This embodiment is illustrated in FIG. 2A. The horizontal flat detection panel 14 is shown positioned on the floor along with the shoes S of a person walking over the detection panel 14. A cross-section of the detection panel is shown in FIG. 2B. As shown, there is one shielded loop-resonator coil 16E to excite the nuclear quadruple resonance frequencies and one high temperature superconductor self-resonant coil 16D for detecting the nuclear quadruple resonance frequencies. Multiple shielded loop-resonator coils and/or high temperature superconductor self-resonant coils can be used when needed. This embodiment provides an efficient method of detecting contraband concealed in a person's shoes without the necessity of removing the shoes from the feet of the person. This is an embodiment in which it is important that a dimension such as the thickness of the container, in the portion that encloses the flat surface detection panel, be kept to a minimum since the person will be asked to step onto or walk over the detection panel.

The embodiments described above can be combined so that the person and the person's shoes can be simultaneously examined for contraband. Two separate detection systems could be used to achieve this, but a single detection system is preferred. In this embodiment the flat surface detection panel is comprised of two parts, one positioned vertically so that a person can stand near to it and one positioned horizontally near to the floor so that a person can stand on or walk over it, whereby the person and the shoes of the person can be simultaneously examined for contraband.

The detection panel can have various forms such that the front or back and both sides of the person to be examined would be encompassed by the detection panel. For instance, the detection panel can consist of a flat surface for the person to be examined to stand near, as described above, as well as a surface on either side of the flat surface that can be used to simultaneously examine the sides of the person.

Figure 3A:
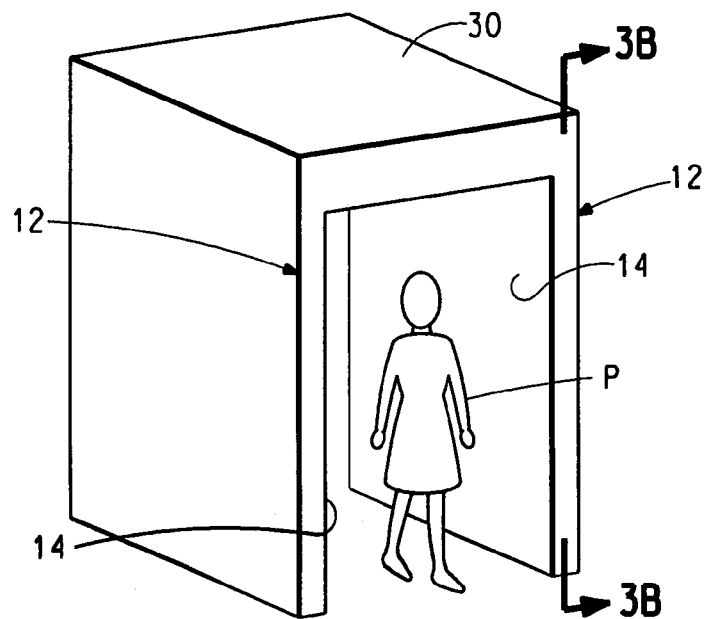
FIGS. 3A and 3B show an embodiment of the present invention implemented in the form of a portal through which a person to be examined passes, with FIG. 3B being a sectional view taken along section lines 3B—3B in FIG. 3A.
Figure 3B:
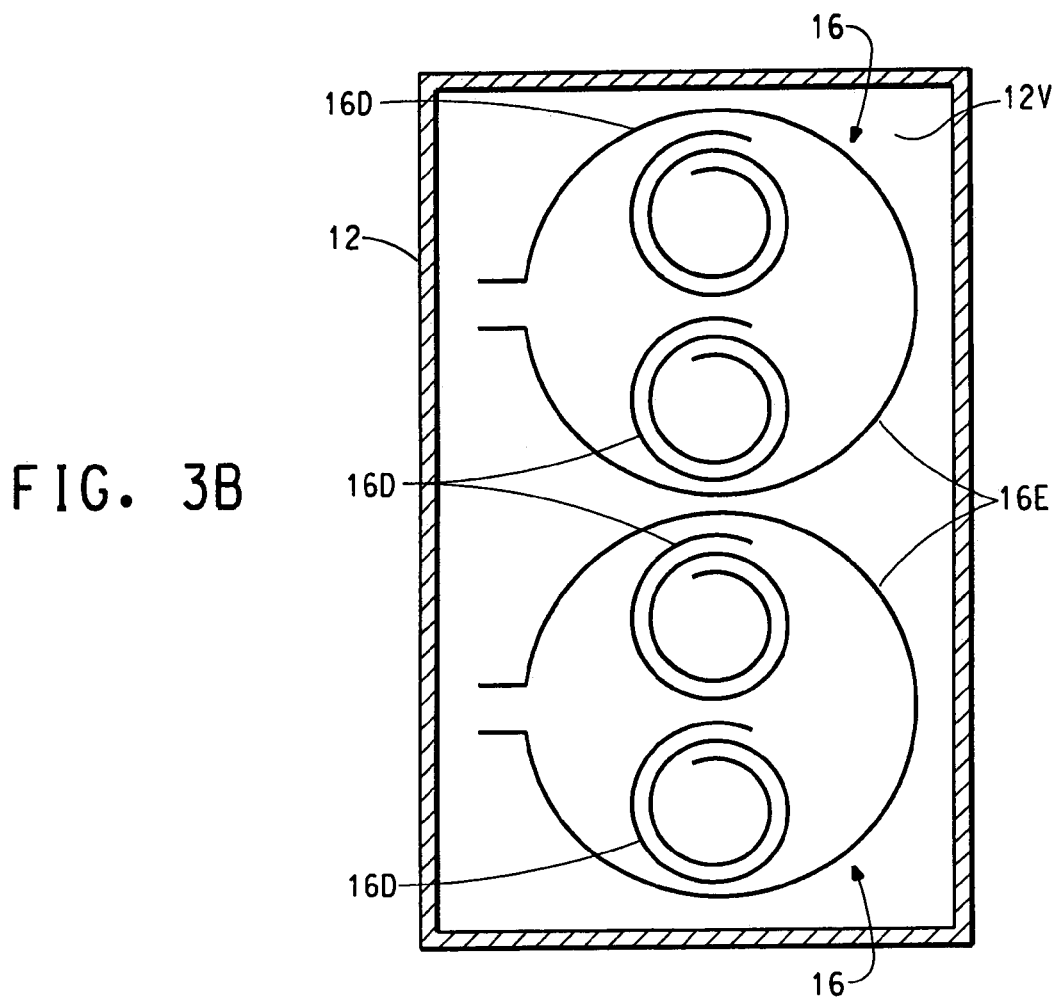

The detection system can also be in the form of a portal through which a person to be examined passes. This is a preferred embodiment since it lends itself to enable a greater throughput of people. The portal must be sufficiently wide to allow a person to pass through yet not so wide as to seriously diminish the detection of the NQR signals. In one embodiment, there is a detection panel on each side of the portal. Preferably, the detection panels are flat surface detection panels. This embodiment is illustrated in FIG. 3A. The portal 30 is shown with a person P to be scanned walking through it. There is a flat surface detection panel 14 on each side of the portal. FIG. 3B shows a cross-section of one of the two identical detection panels. The container 12 having the detection panel 14 contains two shielded loop-resonator coils 16E to excite the nuclear quadrupole resonance frequencies and four high temperature superconductor self-resonant coils 14 for detecting the nuclear quadrupole resonance frequencies. In another embodiment, the detection panel consists of two parts. A flat surface detection panel is positioned horizontally near to the floor at the base of the portal that has the two side detection panels so that a person can stand on or walk over the detection panel, and the person and the person's shoes can be simultaneously examined. In other variations, the detection panel can be elliptical or curved in some other manner to surround three sides of the person to be examined.

In another embodiment, the detection panel can be positioned horizontally at table height, and small objects such as small packages, carry-on luggage, brief cases, handbags and the like can be placed on the detection panel and examined for contraband. A small object as referred to herein is an object with dimensions less than 2d. If the object cannot be completely examined in one position on a particular detection panel, the complete interior of a small object can be examined for contraband by placing the object on the detection panel in various positions. Alternatively, the detection panel can be in the form of a cylinder of diameter equal to 2d, or less than or equal to 2d, and a small object can be passed through the cylinder and completely examined for contraband.

Other embodiments will be useful for examining objects of different shapes and sizes.

What is claimed is:

1. A nuclear quadrupole resonance detection system for detecting contraband, comprising:
    a) a container having a detection panel with an outer surface and an inner surface;
    b) at least one copper or silver shielded loop-resonator coil used solely for exciting the nuclear quadrupole resonance frequencies of a contraband source positioned near the outer surface of the detection panel, wherein the at least one shielded loop-resonator coil is located within the container in close proximity to the inner surface of the detection panel; and
    c) at least one high temperature superconductor coil used solely for detecting the nuclear quadrupole resonance frequencies of the contraband source positioned near the outer surface of the detection panel, wherein the at least one high temperature superconductor coil is a self-resonant planar coil and is located within the container in close proximity to the inner surface of the detection panel.

2. The nuclear quadrupole resonance detection system of claim 1 wherein the shielded loop-resonator coil is a copper shielded loop-resonator coil and the high temperature superconductor coil is a $YBa_2Cu_3O_7$ coil.

3. The nuclear quadrupole resonance detection system of claim 1 or 2, wherein the detection system has a flat surface detection panel.

4. The nuclear quadrupole resonance detection system of claim 3 wherein the flat surface detection panel is positioned vertically to examine for contraband a person standing near to, or passing by, the detection panel.

5. The nuclear quadrupole resonance detection system of claim 3 wherein the flat surface detection panel is positioned horizontally near to the floor to examine for contraband the shoes of a person standing on or walking over the detection panel while the shoes are on the person's feet.

6. The nuclear quadrupole resonance detection system of claim 3 wherein the flat surface detection panel is comprised of two parts, a first part placed vertically so that a person can stand near to or pass by it and a second part placed horizontally near to the floor so that a person can stand on or walk over it, whereby the person and the shoes of the person can be simultaneously examined for contraband.

7. The nuclear quadrupole resonance detection system of claim 3 wherein the flat surface detection panel is positioned horizontally to examine for contraband small objects placed thereon.

8. The nuclear quadrupole resonance detection system of claim 1 or 2, wherein the detection panel surrounds three sides of a person to be examined for contraband.

9. The nuclear quadrupole resonance detection system of claim 1 or 2, wherein the detection system is in the form of a portal through which a person to be examined passes and there is a detection panel on each side of the portal.

10. The nuclear quadrupole resonance detection system of claim 9, wherein the detection panels are flat surface detection panels.

11. The nuclear quadrupole resonance detection system of claim 9, wherein a flat surface detection panel is positioned horizontally near to the floor at the base of the portal so that a person can stand on or walk over the detection panel and the person and the person's shoes can be simultaneously examined.

12. The nuclear quadrupole resonance detection system of claim 1 or 2, wherein the detection panel is in the form of a cylinder of diameter equal to 2d to examine for contraband a small object that is passed through the cylinder, wherein d is the depth of the surface region of the small object within which quadrupole nuclei produce NQR signals that can be detected by a receive coil.

\* \* \* \* \*